US011519876B2

(12) United States Patent
Park et al.

(10) Patent No.: US 11,519,876 B2
(45) Date of Patent: Dec. 6, 2022

(54) ELECTRODE FOR ELECTROCHEMICAL MEASUREMENT

(71) Applicant: NATIONAL UNIVERSITY CORPORATION SHIZUOKA UNIVERSITY, Shizuoka (JP)

(72) Inventors: Enoch Y. Park, Shizuoka (JP); Kenshin Takemura, Shizuoka (JP); Ankan Dutta Chowdhury, Shizuoka (JP)

(73) Assignee: NATIONAL UNIVERSITY CORPORATION SHIZUOKA UNIVERSITY

( * ) Notice: Subject to any disclaimer, the term of this patent is extended or adjusted under 35 U.S.C. 154(b) by 144 days.

(21) Appl. No.: 17/062,653

(22) Filed: Oct. 5, 2020

(65) Prior Publication Data

US 2021/0102912 A1    Apr. 8, 2021

(30) Foreign Application Priority Data

Oct. 7, 2019  (JP) .............................. JP2019-184579
Jul. 28, 2020 (JP) .............................. JP2020-127421

(51) Int. Cl.
*G01N 27/327* (2006.01)
*G01N 27/30* (2006.01)
*G01N 27/417* (2006.01)
*G01N 33/569* (2006.01)

(52) U.S. Cl.
CPC ......... *G01N 27/301* (2013.01); *G01N 27/327* (2013.01); *G01N 27/417* (2013.01); *G01N 33/56983* (2013.01)

(58) Field of Classification Search
CPC .............. G01N 27/301; G01N 27/327; G01N 27/3278; G01N 27/417; G01N 33/56983
See application file for complete search history.

(56) References Cited

FOREIGN PATENT DOCUMENTS

JP        2018-021864 A    2/2018
WO   WO 2013/088367 A1    6/2013

OTHER PUBLICATIONS

Ganganboina et al., "Graphene Quantum Dots Decorated Gold-Polyaniline Nanowire for Impedimetric Detection of Carcinoembryonic Antigen," Scientific Reports (2019) 9:7214 https://doi.org/10.1038/s41598-019-43740-3 with Supplementary Information (Year: 2019).*
Chowdhury et al., "Highly sensitive electrochemical biosensor for glucose, DNA and protein using gold-polyaniline nanocomposites as a common matrix," Sensors and Actuators B 190 (2014) 348-356 (Year: 2014).*
Sargent et al. The electrochemistry of antibody-modified conducting polymer electrodes, Journal of Electroanalytical Chemistry 470 (1999) 144-156 (Year: 1999).*

(Continued)

*Primary Examiner* — Alexander S Noguerola
(74) *Attorney, Agent, or Firm* — Ostrolenk Faber LLP

(57) ABSTRACT

Provided is an electrode for electrochemical measurement for detecting or quantitatively determining a target substance, the electrode comprising: a complex supported on a surface of the electrode, wherein the complex is a complex comprising a probe for the target substance, a quantum dot which binds to the probe and is doped with nitrogen and sulfur, and a conductive polymer nanowire in which a metal nanoparticle is embedded.

1 Claim, 12 Drawing Sheets

Specification includes a Sequence Listing.

(56) References Cited

OTHER PUBLICATIONS

Gamry article entitled "Basics of Electrochemical Impedance Spectroscopy" Downloaded Apr. 23, 2022 from https://www.gamry.com/application-notes/EIS/basics-of-electrochemical-impedance-spectroscopy/ (Year: 2022).*

* cited by examiner

Fig.9

ELECTRODE FOR ELECTROCHEMICAL MEASUREMENT

CROSS-REFERENCE TO RELATED APPLICATION

This application claims priority to Japanese Application No. 2019-184579 filed on Oct. 7, 2019 and Japanese Application No. 2020-127421 filed on Jul. 28, 2020, which are hereby incorporated by reference in its entirety.

TECHNICAL FIELD

The present invention relates to an electrode for electrochemical measurement for detecting a target substance, a biosensor, a method for detecting and quantitatively determining a target substance, and a kit for detecting or quantitatively determining a target substance.

CITATION LIST

Patent Document 1: PCT International Publication No. WO2013/088367

Patent Document 2: Japanese Unexamined Patent Publication No. 2018-21864

BACKGROUND

A method for detecting a virus through RT-PCR which is a technique of performing PCR on cDNA generated using RNA as a template is generally used as a method for detecting a virus. The method using RT-PCR has high sensitivity and can accurately diagnose even subtypes. However, since the method requires advanced technology, it is mainly implemented in public institutions or the like and cannot be performed for examinations in general medical institutions.

An immunoassay which is a measurement method in which a reaction between an antigen and an antibody is used does not require expensive facilities, and therefore, is used in various fields. For example, an immunoassay is used for diagnosing a disease in the medical field and used for measuring pesticide residues in vegetables in the food field. As a representative immunoassay, there is an enzyme-linked immunosorbent assay (ELISA method) which is used for detection of influenza viruses or the like (PCT International Publication No. WO2013/088367).

In addition, a method for binding antibodies against a target substance to gold nanoparticles to detect or quantitatively determine the target substance based on a color reaction of a chromogenic substrate in the presence of hydrogen peroxide due to a peroxidase-like activity of the gold nanoparticles is disclosed in Japanese Unexamined Patent Publication No. 2018-21864.

SUMMARY

An object of the present invention is to detect or quantitatively determine a target substance in a sample with high sensitivity. The present inventors have conducted extensive studies, and as a result, they have found that a target substance can be detected with high sensitivity using an increase in impedance as an index by producing an electrode obtained such that a complex comprising a nanomaterial and a probe is supported on its surface and through electrochemical measurement using the electrode, thus leading to realization of the present invention.

That is, the present invention is as follows.

[1] An electrode for electrochemical measurement for detecting or quantitatively determining a target substance, the electrode comprising: a complex supported on a surface of the electrode, wherein the complex is a complex comprising a probe for the target substance, a quantum dot which binds to the probe and is doped with nitrogen and sulfur, and a conductive polymer nanowire in which a metal nanoparticle is embedded.

[2] The electrode according to [1], wherein the quantum dot is a graphene quantum dot.

[3] The electrode according to [1], wherein the metal nanoparticle is a nanoparticle of at least one metal selected from the group consisting of gold, silver, copper, platinum, cadmium, vanadium, and indium.

[4] The electrode according to [1], wherein the conductive polymer nanowire is polyaniline nanowire.

[5] The electrode according to [1], wherein the probe is an antibody.

[6] The electrode according to [1], wherein the probe is a nucleic acid.

[7] The electrode according to [1], wherein the quantum dot is a graphene quantum dot, the metal nanoparticle is a nanoparticle of at least one metal selected from the group consisting of gold, silver, copper, platinum, cadmium, vanadium, and indium, the conductive polymer nanowire is a polyaniline nanowire, and the probe is an antibody.

[8] The electrode according to [1], wherein the quantum dot is a graphene quantum dot, the metal nanoparticle is a nanoparticle of at least one metal selected from the group consisting of gold, silver, copper, platinum, cadmium, vanadium, and indium, the conductive polymer nanowire is a polyaniline nanowire, and the probe is a nucleic acid.

[9] A biosensor comprising: an electrode system comprising a working electrode and a counter electrode, wherein the working electrode is the electrode according to [1].

[10] A method for detecting or quantitatively determining a target substance in a sample, the method comprising: a step of bringing the sample into contact with a working electrode; and a step of measuring an impedance of the working electrode, wherein the working electrode is the electrode according to [1].

[11] A method for detecting or quantitatively determining a target substance in a sample, the method comprising: a step of bringing the sample into contact with an electrode system comprising a working electrode and a counter electrode to apply a pulse voltage to the electrode system; and a step of measuring an impedance of the working electrode, wherein the working electrode is the electrode according to [1].

[12] The method according to [11], wherein the pulse voltage is 0.2 to 1.2 V.

[13] A kit for detecting or quantitatively determining a target substance, the kit comprising: an electrode comprising a complex supported on its surface, wherein the complex comprises a quantum dot doped with nitrogen and sulfur and a conductive polymer nanowire in which a metal nanoparticle is embedded.

[14] A kit for detecting or quantitatively determining a target substance, the kit comprising: a conductive polymer nanowire in which a metal nanoparticle embedded; and a quantum dot doped with nitrogen and sulfur.

[15] The kit according to [13], wherein the quantum dot is a graphene quantum dot.

[16] The kit according to [14], wherein the quantum dot is a graphene quantum dot.
[17] The kit according to [13], wherein the metal nanoparticle is a nanoparticle of at least one metal selected from the group consisting of gold, silver, copper, platinum, cadmium, vanadium, and indium.
[18] The kit according to [14], wherein the metal nanoparticle is a nanoparticle of at least one metal selected from the group consisting of gold, silver, copper, platinum, cadmium, vanadium, and indium.
[19] The kit according to [13], wherein the conductive polymer nanowire is a polyaniline nanowire.
[20] The kit according to [14], wherein the conductive polymer nanowire is a polyaniline nanowire.

BRIEF DESCRIPTION OF THE DRAWINGS

FIG. 9 is a calibration curve created from impedance change rates of Example 8.

DETAILED DESCRIPTION

Principle

Figure 1:
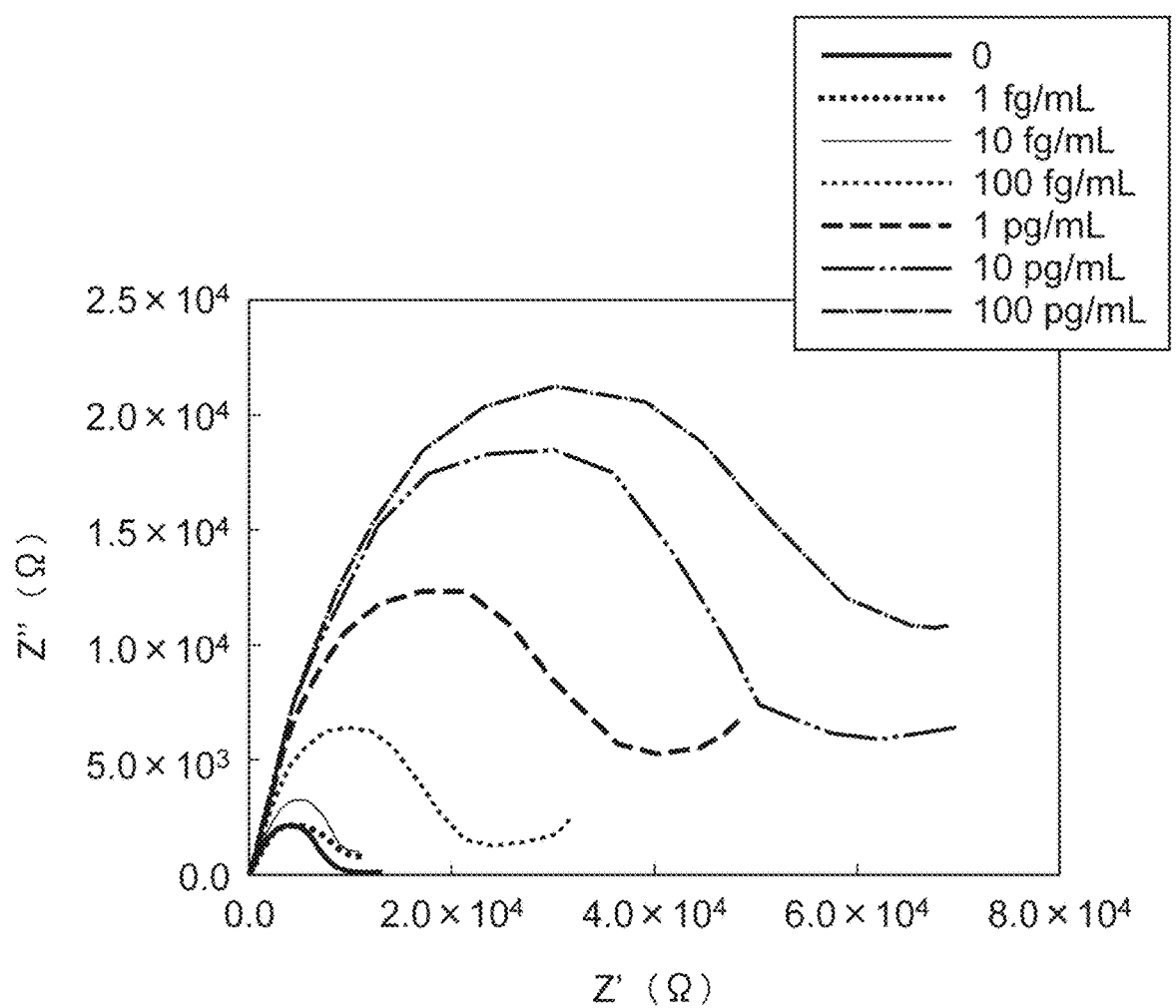
FIG. 1 is a diagram showing an impedance, which is measured in Example 1 and obtained from electrodes immersed in a virus-like particle solution at each concentration, using Nyquist plots.

Although not limited to a specific theory, the present inventors consider that the measurement principle of the present invention is as follows. A complex is supported on the surface of an electrode for electrochemical measurement of the present embodiment. The complex is formed such that a probe for a target substance is fixed to a nanomaterial composite which is formed by combining a plurality of nanomaterials and has a high specific surface area and excellent conductivity. Binding of the target substance to the probe in the complex inhibits electron transfer and increases an impedance of the electrode surface. For this reason, the target substance can be detected or quantitatively determined with high sensitivity through electrochemical measurement using a change in impedance of the electrode surface as an index.

Electrode for Electrochemical Measurement

The electrode for electrochemical measurement of the present embodiment comprises a complex supported on a surface of the electrode, in which the complex comprises a probe for a target substance, a quantum dot which binds to the probe and is doped with nitrogen and sulfur, and a conductive polymer nanowire in which a metal nanoparticle is embedded. Hereinafter, each part constituting the electrode for electrochemical measurement of the present embodiment will be described in detail.

A Probe for A Target Substance

In the detection or quantitative determination method of the present embodiment, "a target substance" to be detected is not particularly limited, and may be substances specifically binding to a probe. For example, one of a set of substances, such as antigen-antibody, sugar-lectin, ligand-receptor, aptamer-target substance of aptamer, or nucleic acid-nucleic acid, specifically binding to each other can be used as a target substance and the other can be used as a probe. For example, viruses, proteins, peptides, DNA, RNA, sugars, chemical substances, or hormones can be used as a target substance or a probe. A probe preferably has a carboxy group from the viewpoint of easy binding to a quantum dot. In addition, it is preferable that a probe be an antibody and a target substance be an antigen to the antibody from the viewpoints of obtaining high specificity and exhibiting excellent sensitivity. Examples of representative viruses diagnosed using specific antibodies comprise hepatitis viruses (types A, B, C, D, E, F, G and TT) which infect humans or non-human animals, influenza viruses, noroviruses, adenoviruses, cytomegaloviruses, white spot syndrome virus (WSSV), coronavirus (comprising 2019-nCoV=SARS-CoV-2), and dengue virus (types 1, 2, 3 and 4).

In a case where a virus is a target substance, an antibody against a surface antigen of the virus can be used as a probe to the target substance. A surface antigen of known viruses can be used, and examples thereof comprise genogroups 1 to 7 (G1 to G7) of hepatitis E virus, hemagglutinin (HA) and neuraminidase (NA) of influenza viruses, norovirus genogroups I and II, and coronavirus spike proteins.

An antibody can be produced through well-known methods. For example, an antibody can be acquired by immunizing animals such as mice, rabbits, or goats with partial sequence peptides in a region specific to a target substance to collect antiserums or by producing hybridomas that produce an antibody. In addition, commercially available an antibody may be used. An antibody may be a polyclonal antibody, a monoclonal antibody, or functional fragments thereof. In addition, one kind or two or more kinds of antibodies against a target substance can be used.

A target substance to be detected or quantitatively determined may be present in a liquid, a solid, powder, a fluid, a gas, or the like. Examples of sample materials comprise urine, stools, blood, other body fluids, mucous membranes, hair, cells, and tissues collected from humans or non-human animals. As will be described below, in the method for detecting or quantitatively determining a target substance of the present invention, a sample is preferably a liquid. Therefore, in a case where a target substance is present in a sample material other than a liquid, it is preferable to dissolve or suspend the sample material in an appropriate buffer or the like to make the sample a liquid.

A Quantum Dot

A quantum dot refers to a nanocrystal having a quantum well structure with a diameter of about 3 to 10 nm. A quantum dot used in the electrode of the present embodiment is not particularly limited. Examples thereof comprise a quantum dot in graphene, zinc, cadmium, lead, indium, and the like, and the quantum dot in graphene is preferable from the viewpoints of excellent conductivity and easy availability. The average particle diameter of the quantum dot is preferably greater than or equal to 4 nm and less than or equal to 10 nm.

The above-described quantum dot is doped with nitrogen and sulfur. By doping the quantum dot with nitrogen, amino groups are more easily added to the quantum dot using a cross-linking agent or the like, and in a case where a probe has carboxy groups, the probe can be simply bound to the quantum dot by bonding of the carboxy groups in the probe to the amino groups in the quantum dot. In addition, by doping the quantum dot with sulfur, metal nanoparticle can be simply bound to sulfur due to affinity between the metal nanoparticles and sulfur. That is, by doping the quantum dot with nitrogen and sulfur, a complex comprising a probe, a quantum dot, and a conductive polymer nanowire in which a metal nanoparticle is embedded can be easily formed.

The method for producing a quantum dot doped with nitrogen and sulfur is not particularly limited. For example, a quantum dot may be synthesized from a substance comprising nitrogen, sulfur, and carbon through a hydrothermal method as shown in examples to be described below. In addition, the quantum dot may be doped with nitrogen and sulfur through a well-known method such as ion implantation or microwave heating.

In the present embodiment, when bonding a probe for a target substance to a quantum dot, or the probe for the target substance may be directly bound to the quantum dot, or the probe for the target substance may be bound to the quantum dot via another probe recognizing the probe for the target substance. The other probe recognizing the probe may be, for example, secondary antibodies against primary antibodies. The bonding of the probe to the quantum dot can be simply performed by adding a well-known cross-linking agent such as an N-ethyl-N'-(3-dimethylaminopropyl)carbodiimide (EDC)/N-hydroxysuccinimide (NHS) reagent to a solution comprising a probe and a quantum dot.

Conductive Polymer Nanowire

In the present specification, a conductive polymer nanowire refers to a fibrous structure which has a diameter of about 10 to 20 nm and has a conductive polymer as a main constituent element. In the present embodiment, a conductive polymer nanowire is intertwined or fused with each other to form a mesh-like or sponge-like structure, and excellent conductivity can be exhibited.

In the present embodiment, a conductive polymer used as a conductive polymer nanowire is not particularly limited as long as it is a polymer having conductivity, and examples thereof comprise a polymer such as polyaniline, polythiophene, polyacetylene, polypyrrole, and poly(p-phenylene vinylene). Among the conductive polymer, polyaniline is preferable as a conductive polymer from the viewpoints of conductivity, easy formation of nanowires, uniformity, and high reproducibility. The above-described conductive polymers can be used alone or in combination of two or more thereof.

A metal nanoparticle to be described below is embedded in the conductive polymer nanowire. Here, in the expression "a metal nanoparticle being embedded in the conductive polymer nanowire", a metal nanoparticle may be comprised inside the conductive polymer nanowire, a metal nanoparticle may be attached onto the fiber surfaces of the conductive polymer nanowire, or metal nanoparticle may be comprised in hole portions of a mesh-like or sponge-like structure formed by the conductive polymer nanowire. In order to support more probes, bound to a quantum dot, on the electrode surface, it is preferable to disperse a metal nanoparticle in or on the conductive polymer nanowire.

The method for producing a conductive polymer nanowire in which a metal nanoparticle is embedded is not particularly limited, but for example, metal ions or metal complexes which become a raw material for a metal nanoparticle can be added to a polymerization solution comprising a monomer which becomes a raw material for a conductive polymer to form a metal nanoparticle simultaneously with polymerization, whereby a conductive polymer nanowire in which the metal nanoparticle is embedded can be produced. The polymerization method may be a well-known polymerization method such as an interfacial polymerization method, a suspension polymerization method, and an emulsion polymerization method. In addition, a conductive polymer nanowire and a metal nanoparticle may be separately produced, and the metal nanoparticle may be attached to the produced conductive polymer nanowire.

A Metal Nanoparticle

In the present specification, a metal nanoparticle means the metal particle having a particle diameter in nano order. The particle diameters of the metal nanoparticle are not particularly limited, but can be, for example, longer than or equal to 1 nm and shorter than or equal to 100 nm.

Metals comprising a metal nanoparticle is not particularly limited, and examples thereof comprise gold, silver, copper, platinum, cadmium, vanadium, and indium. Among these, gold, silver, and platinum are preferable and gold is more preferable from the viewpoints of having high affinity with living bodies and excellent conductivity. These metals may be used alone or in combination of two or more thereof.

In a case where a metal nanoparticle is separately produced from a conductive polymer nanowire, the production method thereof is not particularly limited, and any well-known method can be used. For example, metal ions or metal complexes which become a raw material are reduced with a reducing agent, and aggregated to produce a metal nanoparticle. For example, tetrachloroauric(III) acid is reduced with a reducing agent such as sodium borohydride, citric acid, tannic acid, gallic acid, and isoflavone and aggregated to produce gold nanoparticles. The amounts of the metal nanoparticle and reducing agent to be used can be appropriately determined by those skilled in the art.

When a quantum dot doped with nitrogen or sulfur are added onto a conductive polymer nanowire in which a metal nanoparticle is embedded, the conductive polymer nanowire can be bound to the quantum dot due to affinity between the metal nanoparticle and sulfur. Bonding between a probe and a quantum dot may be performed before or after the bonding between the conductive polymer nanowire and the quantum dot. However, the bonding between the probe and the quantum dot is preferably performed before the bonding between the conductive polymer nanowire and the quantum dot from the viewpoint of production efficiency.

Electrode

The electrode material used for the electrode for electrochemical measurement of the present embodiment is not particularly limited, and well-known electrode materials can be used. Conductive materials such as silicone, carbon, and metals such as platinum, gold, silver, and mercury can be used. In addition, a glass-like electrode, a glass-like carbon electrode, and an electrode made of a composite material such as conductive rubber or conductive carbon paper can be used.

It is preferable that the electrode surface be coated with a conductive polymer before a complex is supported. By performing the coating with a conductive polymer, the above-described complex is easily bound to the electrode due to affinity with a conductive polymer nanowire. The type of conductive polymer used for coating the electrode surface may be the same as or different from the type of conductive polymer constituting a conductive polymer nanowire, but is preferably the same as the type of conductive polymer constituting a conductive polymer nanowire from the viewpoint of affinity.

Method for Producing Electrode

The electrode for electrochemical measurement of the present embodiment can be produced, for example, through the following method. A quantum dot doped with nitrogen and sulfur is used to bind a probe for a target substance to the quantum dot. The quantum dot to which the probe is bound is bound to a conductive polymer nanowire in which a metal nanoparticle is embedded to form a complex comprising the probe, the quantum dot, and the conductive polymer nanowire. By adding the complex onto the electrode surface preferably coated with a conductive polymer, the complex can be physically adsorbed on the electrode surface and supported on the electrode surface to form the electrode for electrochemical measurement of the present embodiment.

Biosensor

The biosensor of the present embodiment comprises the above-described electrode for electrochemical measurement as a working electrode. The "biosensor" in the present specification refers to a measurement system that electrochemically detects or quantitates a target substance using a specific bonding reaction between the probe and the target substance. The biosensor of the present embodiment may be a two-electrode system comprising a working electrode and a counter electrode, or may be a three-electrode system comprising a working electrode, a counter electrode, and a reference electrode. In addition, the biosensor may be provided with a constant temperature cell in which a sample is to be placed, a power source for applying a voltage to an electrode system, a pulse signal source for applying a pulse voltage to the electrode system, an ammeter, an impedance measurement device, and a recorder, and may be a batch type or a flow type. Any well-known constant temperature cells, power sources, pulse signal sources, impedance measurement devices, ammeters, and recorders can be used.

In the biosensor of the present embodiment, the electrode of the above-described embodiment may be used as a working electrode. The counter electrode and the reference electrode are not particularly limited, and any well-known ones can be used. Examples thereof comprise a configuration in which a glass electrode, a carbon electrode, a platinum electrode, or a nickel electrode is used as a counter electrode, and a silver-silver chloride electrode or a silver/silver$^+$ type reference electrode is used as a reference electrode.

According to the electrode for electrochemical measurement of the present embodiment and the biosensor of the present embodiment which comprises the electrode, a target substance can be detected or quantitatively determined with high sensitivity through a detection method or a quantitative determination method to be described below.

Method for Detecting A Target Substance

The method for detecting a target substance of the present embodiment comprises: a step of bringing a sample into contact with a working electrode; and a step of measuring an impedance of the working electrode, in which the above-described electrode for electrochemical measurement is used as the working electrode.

In the method of the present embodiment, detection of a target substance can be performed as follows, for example. A working electrode is brought into contact with a sample by immersing the working electrode in a sample solution. After the elapse of a certain period of time, the working electrode is removed from the sample solution, the electrode is washed, and then, the impedance of the working electrode is measured in a buffer solution. In the present embodiment, in the step of bringing a sample into contact with a working electrode, a pulse voltage may not be applied unlike in another embodiment to be described below.

In the step of bringing a sample into contact with a working electrode, the sample is preferably a liquid from the viewpoint of performing electrochemical measurement. For this reason, it is preferable that the sample material be dissolved or suspended in pure water, a buffer, or the like to make the sample used in the method of the present embodiment a liquid. The sample can be appropriately diluted or concentrated before the measurement.

Examples of buffers for dissolving, suspending, or diluting a sample comprise a phosphate-buffered physiological saline (PBS), (4-(2-hydroxyethyl)-1-piperazineethanesulfonic acid) (HEPES), and 2-morpholinoethanesulfonic acid (MES).

The time over which a working electrode is in contact with a sample is preferably longer than or equal to 180 seconds, more preferably longer than or equal to 10 minutes, and still more preferably longer than or equal to 20 minutes from the viewpoint of sufficiently reacting a probe with a target substance. In addition, the time thereof is preferably shorter than or equal to 1 hour, more preferably shorter than or equal to 30 minutes, and still more preferably shorter than or equal to 20 minutes from the viewpoint of measurement efficiency.

After a sample is brought into contact with a working electrode, an electrode system is removed from the sample, and the impedance of the working electrode is measured in a buffer solution. The working electrode is preferably washed before the measurement of the impedance. The measurement sensitivity can be improved by removing contaminants other than the target substance in the sample which are attached onto the electrode surface. A solution used for washing an electrode is not particularly limited, and is preferably pure water or a buffer such as PBS. When measuring the impedance, the above-described electrode system comprising a working electrode and a counter electrode can be immersed in a buffer solution to measure the impedance.

The measurement of an impedance can be performed through a well-known method. Examples thereof comprise a method such as potential electrochemical impedance spectroscopy (PEIS), and devices usually used as devices for measuring an impedance can be used also in the method of the present embodiment, and commercially available devices may be used for the measurement.

For example, when measuring an impedance through potential electrochemical impedance spectroscopy (PEIS), the frequency range is preferably set to be greater than or equal to 50 mHz and more preferably greater than or equal to 100 mHz, and is preferably set to be less than or equal to 200 kHz and more preferably less than or equal to 100 Hz. In addition, the amplitude is preferably set to be greater than or equal to 2 mV and more preferably greater than or equal to 5 mV, and is preferably set to be less than or equal to 10 mV and more preferably less than or equal to 7 mV. In addition, the time for applying a voltage to an electrode system is preferably longer than or equal to 10 seconds, more preferably longer than or equal to 1 minutes, and still more preferably longer than or equal to 2 minutes from the viewpoint of performing sufficient charge transfer. In addition, the time thereof is preferably shorter than or equal to 0.5 hours, more preferably shorter than or equal to 5 minutes, and still more preferably shorter than or equal to 3 minutes from the viewpoint of measurement efficiency. Within the above-described range, the impedance of a working electrode can be measured with high sensitivity in the method of the present embodiment.

In a case where a target substance is present in a sample, the target substance is bound to a probe on the surface of a working electrode when the working electrode is brought into contact with the sample, charge transfer is inhibited in the working electrode, and the impedance of the working electrode increases. Accordingly, in a case where the impedance of the working electrode is increased compared to an initial impedance of the working electrode before being brought into contact with the sample, it can be determined that the target substance is present in the sample. However, in a case where the impedance of the working electrode is not increased compared to the initial impedance of the working electrode before being brought into contact with the sample, it can be determined that the target substance is not present in the sample. The "impedance of a working electrode" is preferably the impedance of the surface of the working electrode on which a complex is supported.

The initial impedance of a working electrode before being brought into contact with a sample can be measured, for example, by bringing the electrode system into contact with pure water or a buffer instead of the sample with respect to the working electrode before being brought into contact with the sample, that is, the unused working electrode. As the initial impedance of a working electrode, a previously measured value may be used as a reference value, or a value measured for each measurement of a sample may be used.

In the above-described method, the electrode system may be a two-electrode system comprising a working electrode and a counter electrode, or may be a three-electrode system comprising a working electrode, a counter electrode, and a reference electrode. In the above-described method, the above-described electrode for electrochemical measurement is used as a working electrode, and the electrodes respectively exemplified as the counter electrode and the reference electrode used in the above-described biosensor can be similarly used as a counter electrode and a reference electrode. In addition, in the above-described method, a constant temperature cell, a power source, a pulse signal source, an impedance measurement device, an ammeter, a recorder, or the like may be used in addition to the electrode system.

In addition, in another embodiment, the method for detecting a target substance of the present invention comprises: a step of bringing a sample into contact with an electrode system comprising a working electrode and a counter electrode to apply a pulse voltage to the electrode system; and a step of measuring the impedance of the working electrode, in which the above-described electrode for electrochemical measurement is used as the working electrode.

In the above-described method, detection of the target substance can be performed as follows, for example. An electrode system comprising a working electrode and a counter electrode is brought into contact with a sample by immersing the electrode system in a sample solution. A pulse voltage is applied to the electrode system while bringing the sample into contact with the electrode system. When a voltage is applied thereto, a current flows through the electrode system. After the elapse of a certain period of time, the electrode system is removed from the sample solution and washed, and then, the impedance of the working electrode is measured in a buffer solution.

In the present embodiment, by applying a pulse voltage, a bonding reaction between the probe and the target substance is further promoted and the target substance can be detected with higher sensitivity than a case where no pulse voltage is applied. Although the reason why the bonding reaction between the probe and the target substance is promoted in this manner is unclear, the present inventors consider as follows. By applying a pulse voltage, the specific surface area of the conductive polymer nanowire in a complex supported on an electrode surface is expanded, the probe is dispersed on the electrode surface. Accordingly, since the probe is widely distributed on the electrode surface, the probe can be bound to many target substances, whereby a bonding reaction is promoted.

The pulse voltage to be applied is preferably greater than or equal to 0.2 V, more preferably greater than or equal to 0.4 V, and still more preferably greater than or equal to 0.8 V from the viewpoint of electrochemical characteristics of the polyaniline nanowire. In addition, the pulse voltage to be applied is preferably less than or equal to 1.2 V, more preferably less than or equal to 1.0 V, and still more preferably less than or equal to 0.9 V. That is, the range of the pulse voltage is preferably 0.2 to 1.2 V, more preferably 0.4 to 1.0 V, and still more preferably 0.8 to 0.9 V.

In addition, the time for applying a pulse voltage is preferably longer than or equal to 60 seconds, more preferably longer than or equal to 120 seconds, and still more preferably longer than or equal to 3 minutes. In addition, the time thereof is preferably shorter than or equal to 20 minutes, more preferably shorter than or equal to 10 minutes, and still more preferably shorter than or equal to 5 minutes. That is, the range of the time thereof is preferably 60 seconds to 20 minutes, more preferably 2 minutes to 10 minutes, and still more preferably 3 minutes to 5 minutes.

The length of the time required for bringing a sample into contact with a working electrode is the same as that in the embodiment in the case where no pulse voltage is applied. That is, the time over which an electrode system is in contact with a sample is preferably longer than or equal to 180 seconds, more preferably longer than or equal to 10 minutes, and still more preferably longer than or equal to 20 minutes from the viewpoint of sufficiently reacting a probe with a target substance. In addition, the time thereof is preferably shorter than or equal to 1 hour, more preferably shorter than or equal to 30 minutes, and still more preferably shorter than or equal to 20 minutes from the viewpoint of measurement efficiency.

After a pulse voltage is applied, an electrode system is removed from a sample, and the impedance of a working electrode is measured in a buffer solution. The working electrode is preferably washed before the measurement of the impedance in the same manner as in the embodiment in the case where no pulse voltage is applied.

The measurement of an impedance of a working electrode can be performed in the same manner as in the embodiment in the case where no pulse voltage is applied. In a case where the impedance of the working electrode is increased compared to an initial impedance of the working electrode before being brought into contact with the sample, it can be determined that the target substance is present in the sample. However, in a case where the impedance of the working electrode is not increased compared to the initial impedance of the working electrode before being brought into contact with the sample, it can be determined that the target substance is not present in the sample.

Also in the present embodiment, the electrode system exemplified in the embodiment in the case where no pulse voltage is applied can be similarly used as an electrode system. In addition, a constant temperature cell, a power source, a pulse signal source, an impedance measurement device, an ammeter, a recorder, or the like may be used in addition to the electrode system.

Method for Quantitatively Determining A Target Substance

In the method for quantitatively determining a target substance of the present embodiment, the process up to a step of measuring an impedance of a working electrode is the same as that of the method for detecting a target substance. In the quantitative determination method, it is possible to quantitatively determine a target substance in a sample using a calibration curve created based on impedance change rates of a working electrode brought into contact with target samples comprising a target substance with a known concentration. The quantitative determination using a calibration curve can be performed through a general method. For example, a calibration curve is previously created from an impedance change rate of the working electrode brought into contact with a plurality of target samples comprising a target substance with a known concentration, and the measured impedance change rates are applied to this calibration curve, whereby the concentration of a target substance in the samples can be obtained.

An impedance change rate refers to a ratio of impedance of a working electrode after being brought into contact with a sample to an initial impedance of the working electrode before being brought into contact with the sample, and can be obtained by the following equation, for example.

Impedance change rate={(impedance of working electrode after being brought into contact with sample)/(initial impedance of working electrode before being brought into contact with sample)}×100(%)

Kit

In one embodiment, a kit for detecting or quantitatively determining a target substance comprises an electrode comprising a complex supported on its surface, and the complex is a complex comprising a quantum dot doped with nitrogen and sulfur, and a conductive polymer nanowire in which a metal nanoparticle is embedded. A probe may not be bound to the complex in the kit, and in this case, a user can produce an electrode by binding the probe for a target substance to a quantum dot in the complex by himself or herself. Such a kit has an advantage that a probe can be freely selected according to a target substance. The kit may comprise a reagent for binding a probe to a quantum dot in a complex, and examples of such reagents comprise a well-known cross-linking agent such as an EDC/NHS reagent. Those described above can be suitably used as the electrode, the quantum dot doped with nitrogen or sulfur, and the conductive polymer nanowire in which a metal nanoparticle is embedded. The kit may further comprises an attached document in which the method for detecting or quantitatively determining a target substance using the kit is described in addition to a cleanser, a buffer, a constant temperature cell, a power source, a pulse signal source, an impedance measurement device, an ammeter, a recorder, and the like.

In another embodiment, a kit for detecting or quantitatively determining a target substance comprises: a conductive polymer nanowire in which a metal nanoparticle is embedded; and a quantum dot doped with nitrogen or sulfur. The kit may not comprise an electrode and a probe. In this case, a user can prepare an electrode and a probe for a target substance, produce the above-described complex comprising a probe for a target substance, a quantum dot which binds to the probe and is doped with nitrogen and sulfur, and a conductive polymer nanowire in which a metal nanoparticles is embedded, and binds the electrode to the complex. Such a kit has an advantage that a probe can be freely selected according to a target substance and an advantage that an electrode can be freely selected according to a use environment, the price, or the like. The kit may comprise a reagent for binding the probe to the quantum dot in a complex similarly to the above-described kit. In addition, in order to bind an electrode to a complex, the electrode may comprise a coating agent or the like for performing coating, and examples of such coating agents comprise a conductive polymer of the same kind as those of the conductive polymer nanowires, monomers constituting the polymer, and a cross-linking agent. Those described above can be suitably used as the quantum dot doped with nitrogen or sulfur and the conductive polymer nanowire in which a metal nanoparticle is embedded. The kit may further comprise, similarly to the above-described kit, an attached document in which the method for detecting or quantitatively determining a target substance using the kit is described in addition to a cleanser, a buffer, a constant temperature cell, a power source, a pulse signal source, an impedance measurement device, an ammeter, a recorder, and the like.

EXAMPLES

Production of Electrode

Synthesis of Polyaniline Nanofibers in which Gold Nanoparticles are Embedded

Synthesis of polyaniline nanofibers in which gold nanoparticles are embedded is performed through an interfacial polymerization method. 0.1 M hydrochloric acid (aqueous layer) in which 3 mM tetrachloroauric(III) acid ($HAuCl_4$) was dissolved was slowly added to a solution (organic layer) in which 0.5 M aniline was dissolved in toluene so that an interface was not disturbed, and the mixture was allowed to stand at room temperature to induce interfacial polymerization of aniline Polyaniline was gently formed in the aqueous layer, and gold ions were reduced in this process to form gold nanoparticles in polyaniline. After 4 hours, the aqueous layer turned dark green was subjected to centrifugation (5,500 g, room temperature) and purified through removal of a supernatant and redispersion in ultrapure water. This purification process was repeated 3 times to obtain a solution of polyaniline nanofibers (AuNP/PAni) in which gold nanoparticles are embedded.

Production of Quantum Dots Doped with Nitrogen or Sulfur

Graphene quantum dots doped with nitrogen and sulfur were synthesized through a hydrothermal method in which thiourea and citric acid were used, as follows. 0.23 g of citric acid and 0.23 g of thiourea were dissolved in 5 mL of deionized water, the dissolved mixture was added to a Teflon (registered trademark) lined stainless steel autoclave tube to produce a solution. The solution was heated (at 140° C. for 4 hours) to obtain a brown mixed solution comprising graphene quantum dots doped with nitrogen and sulfur. An ethanol solution was added thereto, and an excess reagent was removed through centrifugation (5,000 g, 5 minutes). As a final stage, dialysis was performed for 8 hours with a 1 kD dialysis bag to obtain highly pure and uniform-sized graphene quantum dots (N,S-GQD) doped with nitrogen and sulfur.

Analysis of AuNP/PAni and GQD Produced

AuNP/PAni and N,S-GQD produced above were observed with a transmission electron microscope (TEM). Gold nanoparticles were specifically observed inside the polyaniline nanowires. Monodispersed nanoparticles were checked in the quantum dots. It was confirmed from particle diameters measured from TEM images that the gold nanoparticles having particle diameters of about 10 to 14 nm and the quantum dots having particle diameters of about 4 to 6 nm were formed.

Production of Virus-Specific Antibodies and Bonding Between Antibodies and Quantum Dots Antibodies were produced using target substances as genotype 3 (G3) hepatitis E virus-like particles. A rabbit was immunized with G3 hepatitis E virus-like particles, and blood was collected from the rabbit. The collected blood was purified with a protein G column to obtain rabbit anti-G3 hepatitis E virus-like particle IgG antibodies. Antibody-bound quantum dots were produced by binding amino groups held by quantum dots doped with nitrogen or sulfur to carboxy groups of the antibodies through a reaction between N-ethyl-N'-(3-dimethylaminopropyl)carbodiimide (EDC) and N-hydroxysuccinimide (NHS).

Production of Complex

The produced antibody-bound quantum dots of which the surfaces were doped with sulfur molecules which have high affinity with gold. Accordingly, by mixing the polyaniline nanofibers, which were synthesized as described above and in which gold nanoparticles were embedded, with the antibody-bound quantum dots, bonding between the antibody-bound quantum dots and the gold nanoparticles was induced to produce a complex (Ab-GQD-AuNP/PAni) comprising the antibody-bound quantum dots and the polyaniline nanowires in which the gold nanoparticles were embedded.

Physical, Optical Analysis of Complex

The produced complex was observed with a high-resolution electron microscope (HR-TEM), and as a result, a plurality of particles were observed in a site where there are gold nanoparticles in the polyaniline nanowires. In order to indicate that these particles are quantum dots, the width of vertical lines (fringes) on the nanoparticles was analyzed using HR-TEM. As a result, 0.21 nm fringes characteristic of graphene quantum dots and 0.24 nm fringes characteristic of gold nanoparticles were present in close proximity. The photoelectron kinetic energy of the gold nanoparticles was analyzed through X-ray spectroscopy. As a result, it was confirmed that the Au 4f peak checked in the polyaniline nanowires in which the gold nanoparticles were embedded was shifted to a high-energy side in the produced complex. This suggests that the gold nanoparticles were bound to the quantum dots through a gold-sulfur affinity bond in the complex.

Production of Electrode for Detecting Virus

In order to immobilize the complex produced above on a glass-like carbon electrode, a polyaniline layer was formed on the electrode as follows. A glass-like carbon electrode was immobilized with a solution obtained by mixing 0.5 M sulfuric acid and 0.1 M aniline monomers with ultrapure water, and the polyaniline layer was deposited on the electrode through a cyclic voltammetry (CV) redox reaction in which a three-electrode system was used. For CV, 10 cycles were performed at a scanning speed of 20 mV/s in a potential range of 0 to 1 V. 10 μL of a solution of the complex (Ab-GQD-AuNP/PAni) produced above was added dropwise to the polyaniline layer deposited on the electrode to produce an electrode for detecting a virus.

Electrochemical Detection of Virus

Example 1

Detection of Hepatitis E Virus-Like Particles

Hepatitis E virus-like particles (HEV-LPs) produced using genotype 3 were used as target substances. Solutions obtained by suspending virus-like particles in phosphate-buffered physiological saline (PBS) at seven concentrations from 1 fg/mL to 1 ng/mL were prepared, and detection was performed as follows. Using the electrode for detecting a virus was used as a working electrode, the working electrode was immersed in each solution and incubated for 5 minutes. The working electrode was washed by gently adding dropwise ultrapure water thereto to remove the virus solution. In order to measure an increase in electrical resistance value due to virus bonding onto the working electrode, an impedance ($R_{ct}$) was measured through CV and a potential electrochemical impedance spectroscopy (PEIS) mode. PEIS was performed with a sine wave amplitude of 5 mV from 100 kHz to 0.1 Hz.

Examples 2 and 3

Detection of Hepatitis E Virus-Like Particles (Pulse Voltage Application)

Detection of hepatitis E virus-like particles was performed (Examples 2 and 3) in the same manner as in Example 1 except that a working electrode and a counter electrode were immersed in each solution and an external electromagnetic pulse was applied thereto for 5 minutes through chronoamperometry (CA). A pulse voltage of +0.8 V was applied in Example 2, and a pulse voltage of 1.2 V was applied in Example 3.

Figure 2:
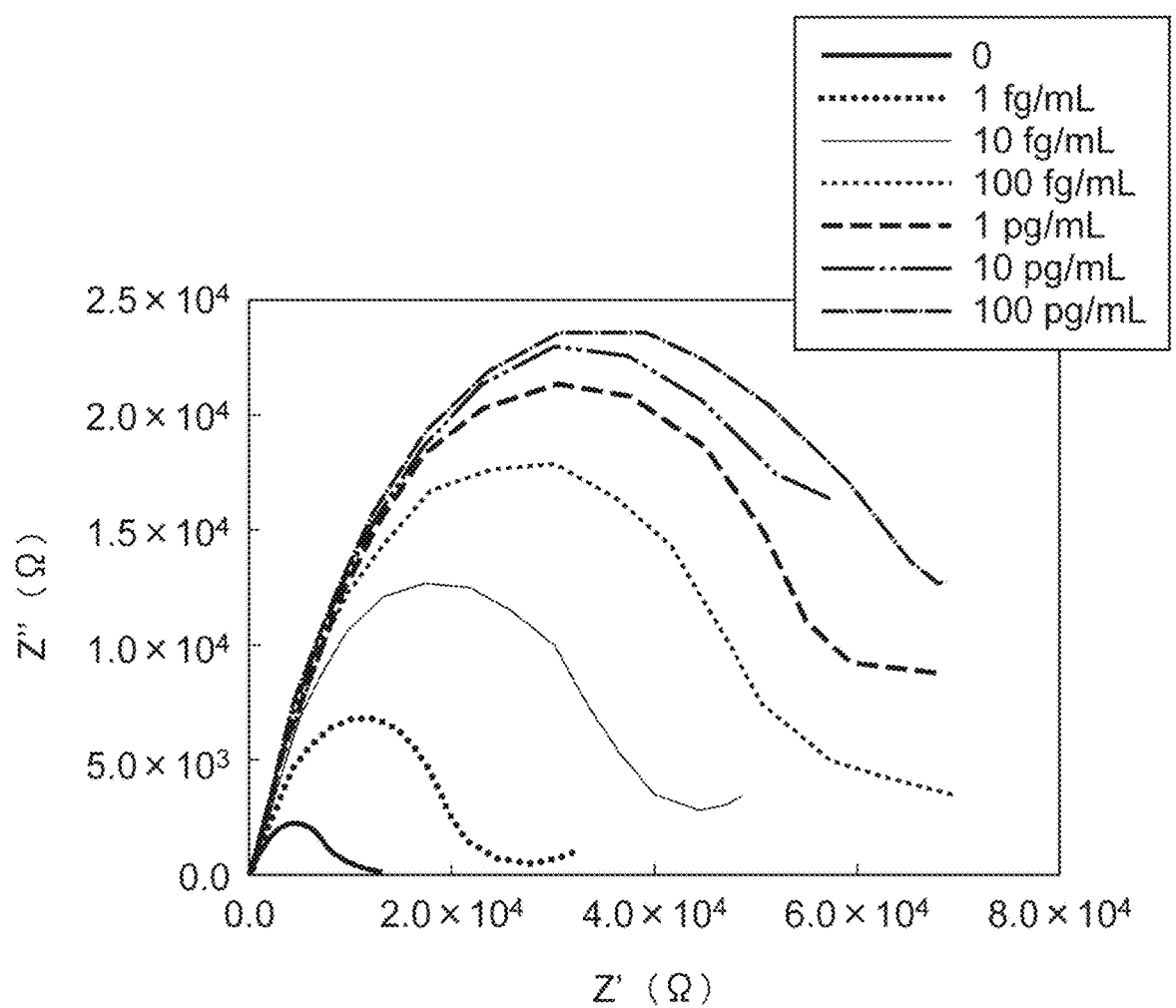
FIG. 2 is a diagram showing an impedance, which is measured in Example 2 and obtained from electrodes immersed in a virus-like particle solution at each concentration, using Nyquist plots.
Figure 3:
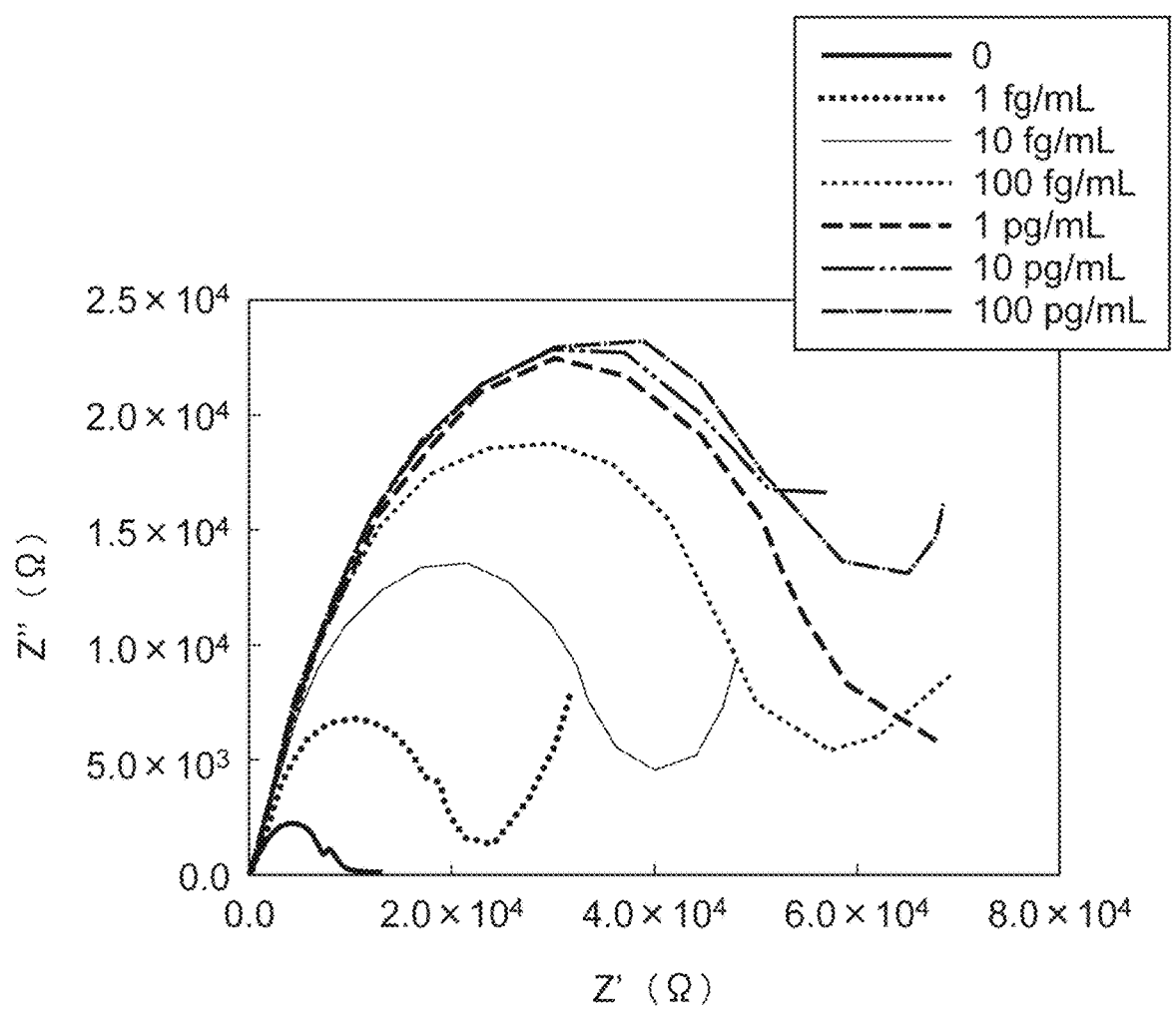
FIG. 3 is a diagram showing an impedance, which is measured in Example 3 and obtained from electrodes immersed in a virus-like particle solution at each concentration, using Nyquist plots.

FIGS. 1 to 3 show impedances, which were respectively measured in Examples 1 to 3 and obtained from electrodes immersed in a virus-like particle solution at each concentration, using Nyquist plots. The horizontal axis shows real number components of impedances, and the vertical axis shows imaginary number components of impedances. As shown in FIGS. 1 to 3, the impedance increased as the concentration of virus-like particles increased.

Figure 4:
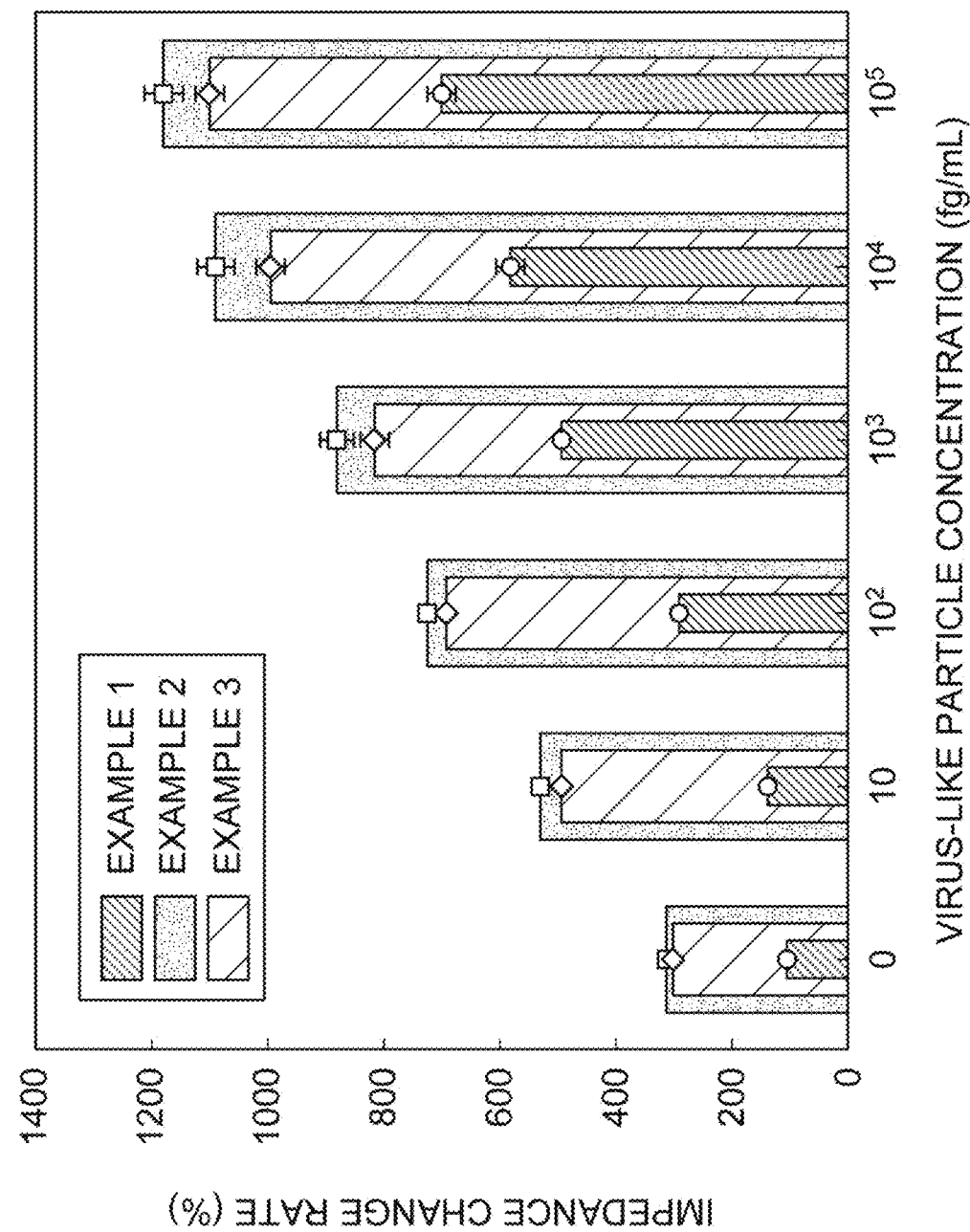
FIG. 4 is a graph showing an impedance change rates of Examples 1 to 3 for each concentration of virus-like particles in solutions.

FIG. 4 is a graph showing impedance change rates of Examples 1 to 3 for each concentration of virus-like particles in solutions. In FIG. 4, the horizontal axis shows concentrations of virus-like particles, and the vertical axis shows impedance change rates. As shown in FIG. 4, the impedance change rates in Examples 2 and 3 in which a pulse voltage was applied were higher than those in Example 1, and even in the low concentration (less than or equal to $10^2$ fg/mL) regions, the difference in impedance change rates depending on the concentration could be clearly read in Examples 2 and 3 in which a pulse voltage was applied.

Figure 5:
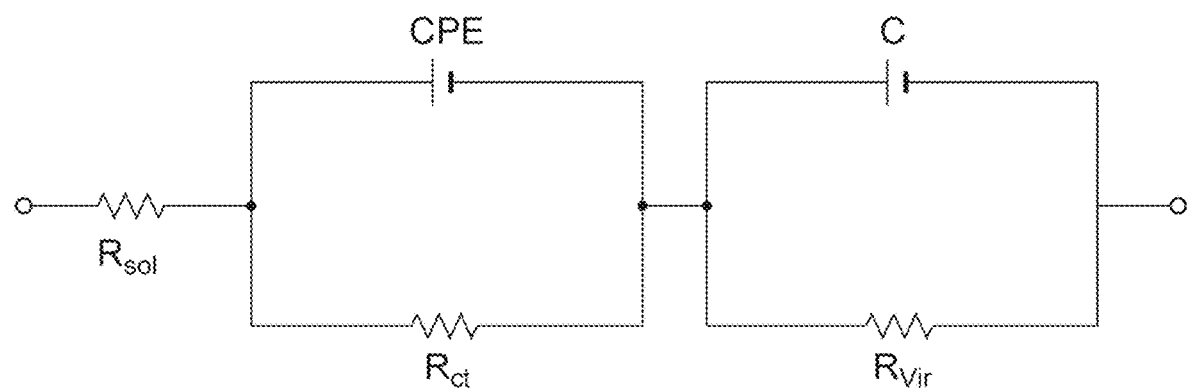
FIG. 5 is a diagram showing an electronic circuit design (equivalent circuit) comprising an impedance.

FIG. 5 shows an electronic circuit design (equivalent circuit) which has been obtained from Nyquist plots and comprises an impedance. In FIG. 5, $R_{sol}$ represents a solution resistance, $R_{ct}$ represents an impedance of the surface of a working electrode, $R_{vir}$ represents an impedance of a target substance layer in a case where the target substance is bound, CPE represents double layer capacitance, and C represents a capacitance. The impedance change rates shown in FIGS. 1 to 4 and 6 are impedance change rates of the surface of a working electrode.

Figure 6:
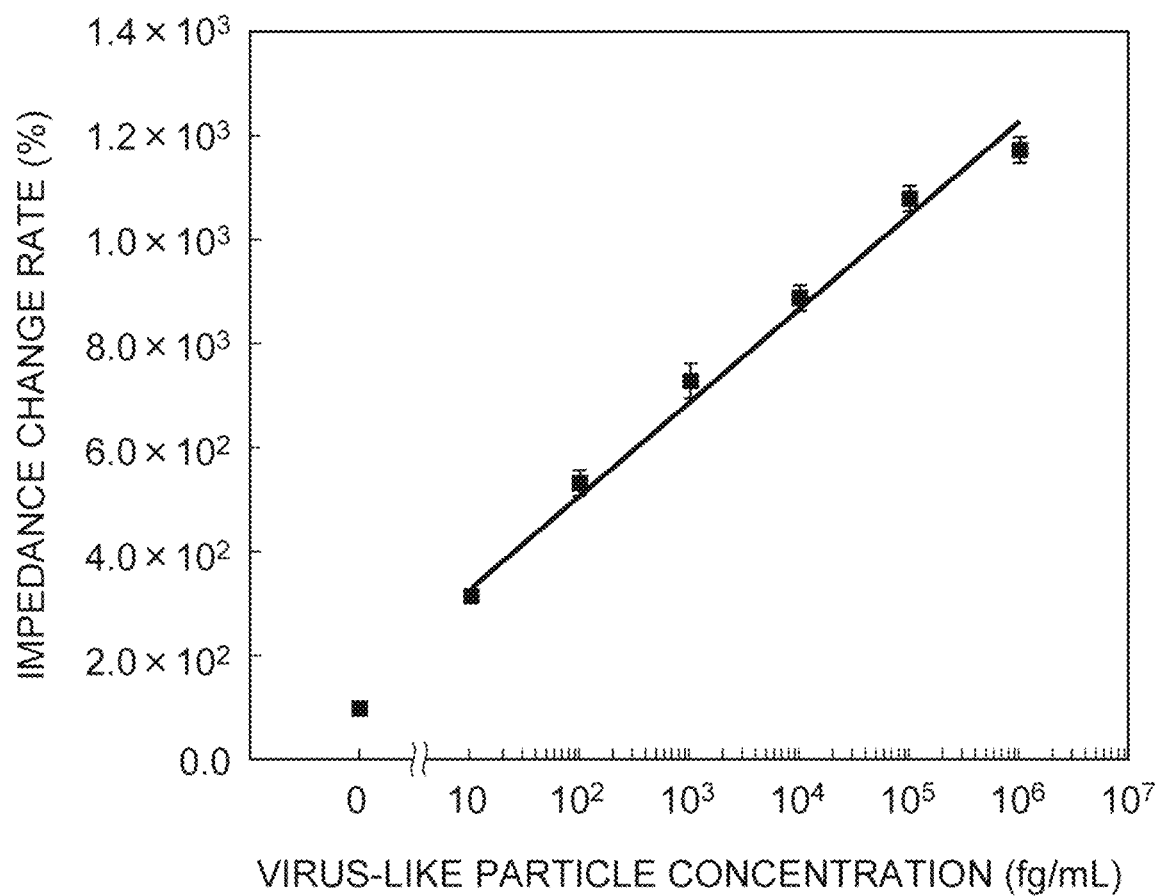
FIG. 6 is a calibration curve created from the impedance change rates of Example 2.

In addition, a calibration curve created from the impedance change rates of Example 2 in which the difference in impedance change rates according to the change in concentration of virus-like particles was particularly large is shown in FIG. 6. In FIG. 6, the horizontal axis shows concentrations (logarithmic values) of virus-like particle solutions, and the vertical axis shows impedance change rates. In the calibration curve, a favorable linear relationship between the impedance change rates and the logarithmic values of the concentrations of virus-like particles was obtained ($R^2=0.9904$). The detection limit of this detection system which was calculated from the calibration curve was 0.8 fg/mL, and was 1,000 times or more of the sensitivity compared to the detection limit in ng/mL order of the ELISA method in the related art.

Example 4

Confirmation of Selectivity of Detection System

Detection of two kinds of influenza strains (H1N1 and H9N2), Zika virus, and norovirus was performed using the electrode produced above. A solution comprising a virus at a concentration of 10 pg/mL was prepared for each virus, and an impedance of each solution was measured through the same method as that in Example 2. As a result, no increase in impedance of a working electrode was shown even if each of the viruses, two kinds of influenza strains (H1N1 and H9N2), Zika virus, and norovirus, was brought into contact with the working electrode, and therefore, it was confirmed that the produced electrode can be used for specifically detecting hepatitis E virus.

Example 5

Confirmation of Stability of Detection System

A solution obtained by suspending hepatitis E virus-like particles in 50% human serum solution at 6 kinds of concentrations from 10 fg/mL to 1 ng/mL was prepared, and detection was performed through the same method as that in Example 2. As a result, no increase in impedance of a working electrode brought into contact with a negative control (50% human serum solution) which did not comprise virus-like particles was confirmed, and it was confirmed that nonspecific adsorption of contaminant proteins on the electrode did not occur. In addition, the impedance change rate was increased in a virus-like particle concentration-dependent manner in the working electrode brought into contact with the human serum solution comprising virus-like particles. Accordingly, it was shown that this detection system can selectively detect a target substance even in a solution comprising a large amount of contaminants.

Example 6

Detection of Hepatitis E Virus

Hepatitis E viruses of genotype 1 (G1), genotype 3 (G3), genotype 7 (G7), and ferrets were used as target substances. Hepatitis E viruses of G1, G3, G7, and ferrets were produced through cell culture of human hepatoma cell lines PLC/PRF/5 (JCRB0406, Human Science Research Resources Bank). PLC/PRF/5 cells were cultured in a Dulbecco's modified eagle medium (DMEM) to which heat-inactivated fetal bovine serum (FBS) was added, 1 mL of a 10% stool suspension sample was inoculated onto the PLC/PRF/5 cells, which were then cultured at 36° C. using a maintenance medium. The medium was changed every 4 days, and cell culture supernatants were used for experiments. The RNA copy numbers of hepatitis E virus of G1, G3, G7, and ferrets in the cell culture supernatants were measured through quantitative RT-PCR (RT-qPCR), and as a result, these were respectively $3.7\times10^8$ copies/mL, $1.8\times10^8$ copies/mL, $5.0\times10^8$ copies/mL, and $4.8\times10^8$ copies/mL.

Figure 7:
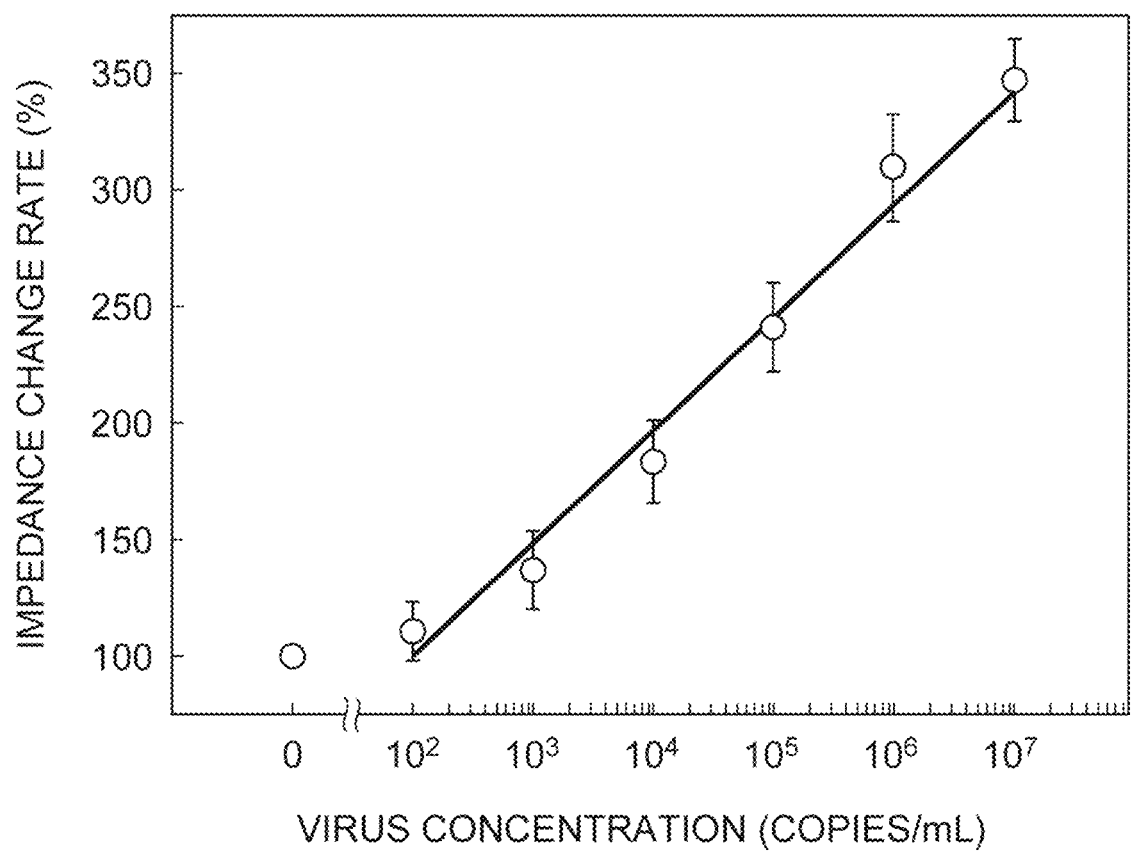
FIG. 7 is a graph showing an impedance change rates with respect to a change in concentration of genotype 3 hepatitis E virus measured in Example 6.

An impedance of each working electrode was measured in the same procedure as in Example 2 except that the above-described cell culture supernatants were used as samples. There was a tendency that an impedance of each working electrode increased in accordance with an increase in concentrations of hepatitis E viruses of G1, G3, G7, and ferrets. FIG. 7 shows impedance change rates of G3 hepatitis E virus with respect to the change in the concentrations. The calibration curve showed linearity in a wide concentration range of $10^2$ to $10^7$ copies/mL ($R^2=0.987$), and the detection limit was 96.7 copies/mL Antibodies comprised in complexes of the working electrodes used in Example 6 were rabbit anti-G3 hepatitis E virus-like particle IgG antibodies similarly to Examples 1 to 5.

Example 7

Detection of Hepatitis E Virus from Clinical Sample

Hepatitis E virus was detected from fecal specimens of a G7 hepatitis E virus-infected crab-eating macaque. Non-human primates comprising crab-eating macaques are widely used as animal models for studies of hepatitis E virus infection and its etiology and vaccine tests. 19 fecal specimens were collected from the G7 hepatitis E virus-infected crab-eating macaque on days 4 to 43 after the infection. The fecal specimens were diluted with 10 mM PBS to prepare a 10% (w/v) suspension. Next, the suspension was shaken at 4° C. for 1 hour, clarified through centrifugation (10,000 g, 30 minutes), passed through a 0.45 µm membrane filter (Millipore, Bedford, Mass.), and preserved at −80° C. until it is used. The virus was inactivated through incubating at 70° C. for 20 minutes, and then, an impedance was measured in the same manner as in Example 2. In addition, the number of pieces of viral RNA was also quantitatively determined through RT-qPCR.

Hepatitis E virus RNA was detected in the fecal specimens on days 4 to 22 after the infection, through RT-qPCR. Since hepatitis E virus RNA was not detected from fecal specimens collected on days 25, 31, 33, and 43 after the infection in the RT-qPCR, these specimens were treated as negative controls. A cutoff value of an impedance was calculated as 1,841Ω based on the impedance of the samples of the negative controls.

Figure 8:
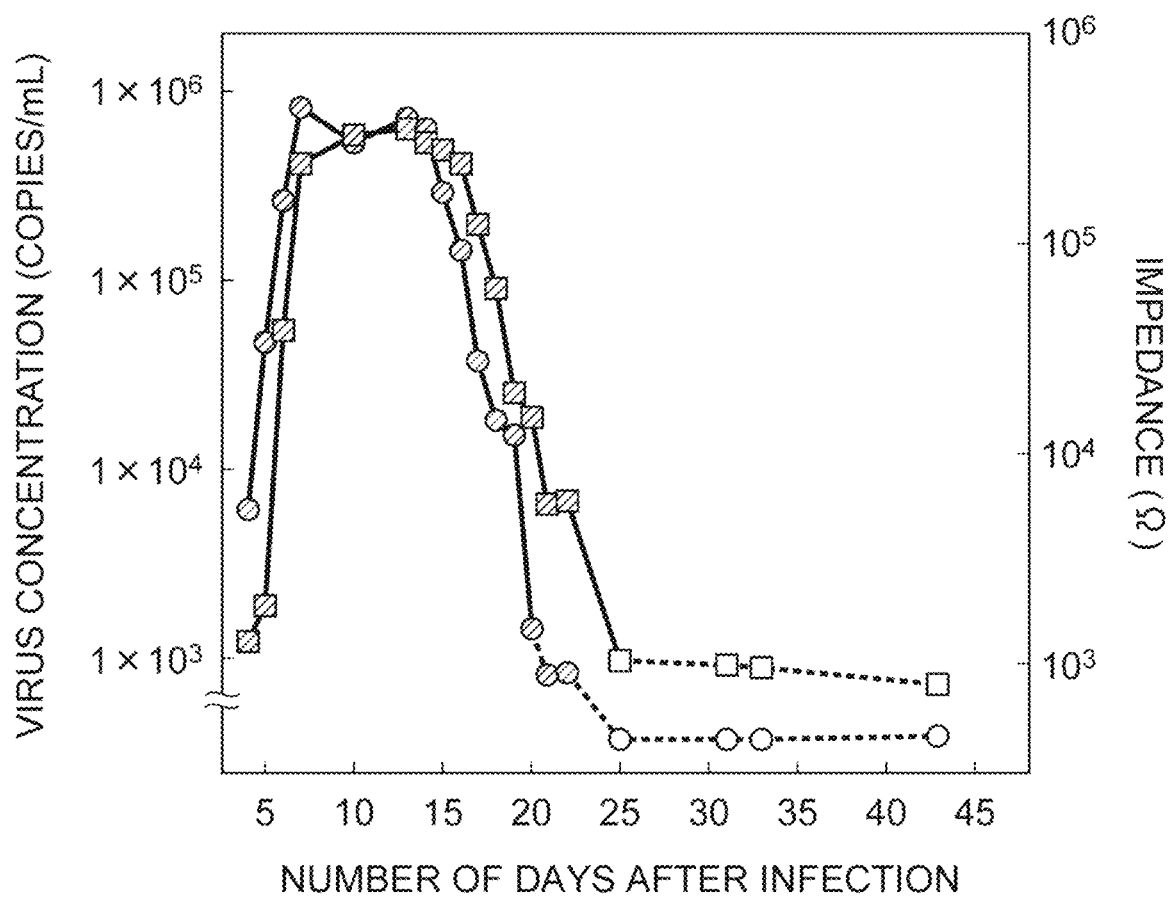
FIG. 8 is a graph showing an impedance value (square) and the number of pieces of viral RNA (circle) which are measured in Example 7.

FIG. 8 shows impedance values (squares) measured through the method of the present embodiment and viral RNA numbers (circles) quantitatively determined through RT-qPCR. The horizontal axis shows the number of post-infection days after the specimens are collected. The fecal specimens on days 25, 31, 33, and 43 after the infection which are negative controls are shown by open squares and open circles in the drawing. As shown in FIG. 8, the graph showing the amount of viral RNA measured through RT-qPCR and the graph showing the impedance values measured through the method of the present embodiment approximately overlap each other, and this shows that the sensitivity of the method of the present embodiment is comparable with the sensitivity of RT-qPCR.

Example 8

Detection of Coronavirus

Figure 9:
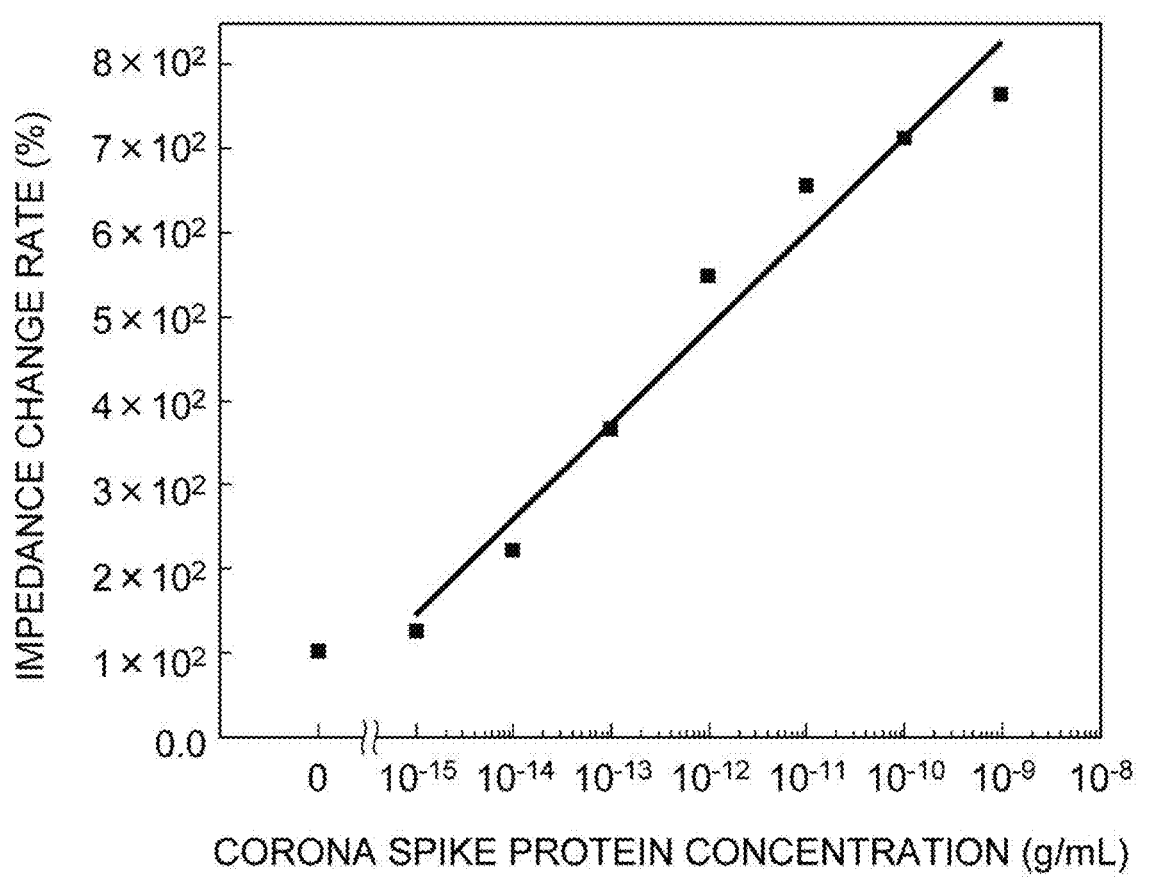

Antibody-bound quantum dots in which Anti-2019-nCoV S Protein Monoclonal Antibody (Cat No. ABN9306, Abvigen Inc., NJ, USA) was used instead of the rabbit anti-G3 hepatitis E virus-like particle IgG antibodies in <Production of Electrode> of the above-described examples were prepared to prepare an electrode for detecting a virus. Recombinant 2019-nCov Spike Protein (Cat No. ABL-1-113, Abvigen Inc., NJ, USA) was used as a specimen. Results obtained by performing detection in dilution series of the specimen at concentrations of 1 fg/mL to 1 ng/mL are shown in FIG. 9. Impedance change rates of 2019-nCov Spike Protein with respect to the change in the concentrations are shown in FIG. 9. The calibration curve showed linearity in the range of the measured concentrations ($R^2=0.96$), and the detection limit was 12.6 fg/mL.

Example 9

Detection of Dengue Virus

Figure 10:
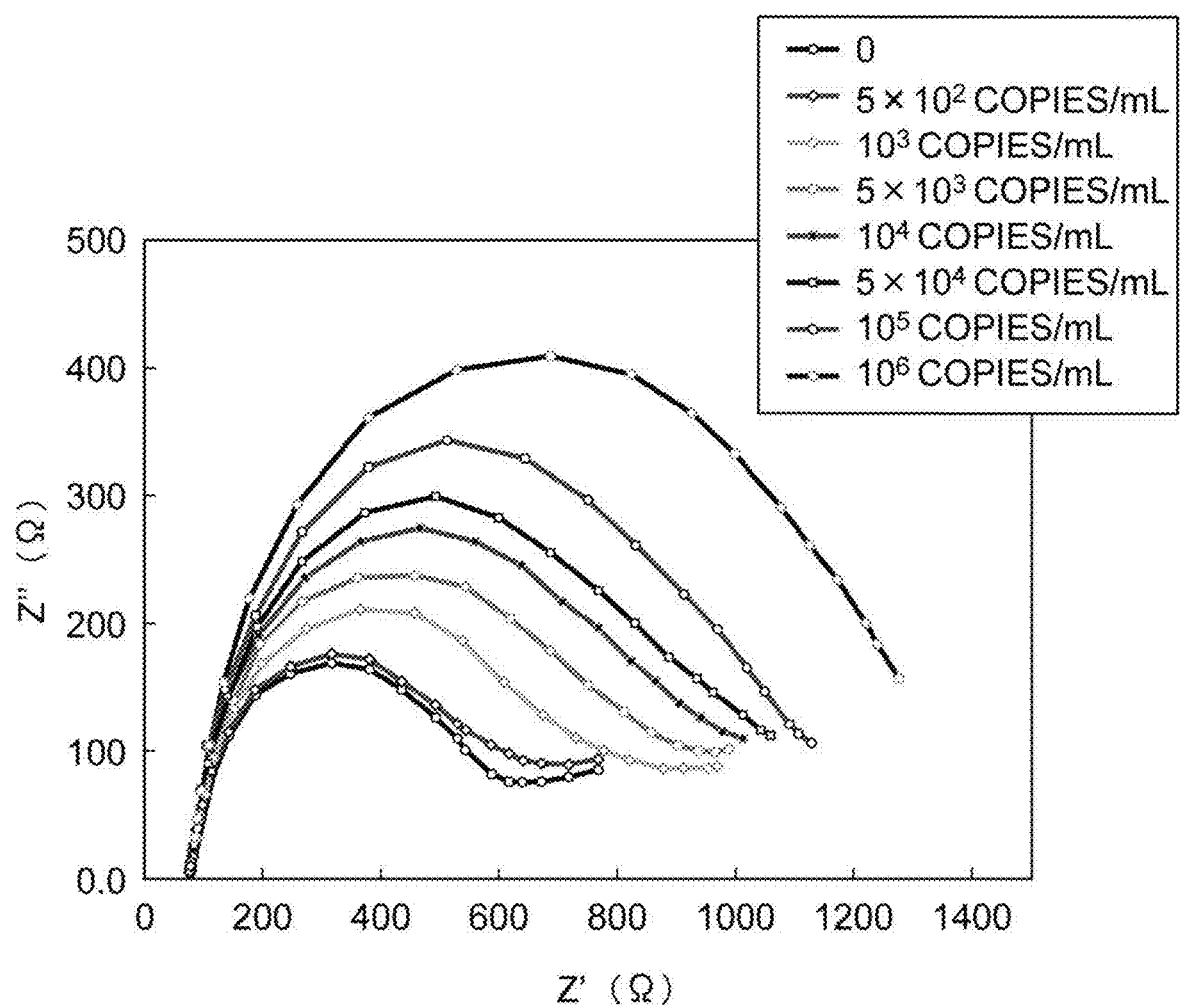
FIG. 10 is a diagram showing an impedance, which is measured in Example 9 and obtained from electrodes immersed in a DNA solution at each concentration, using Nyquist plots.
Figure 11:
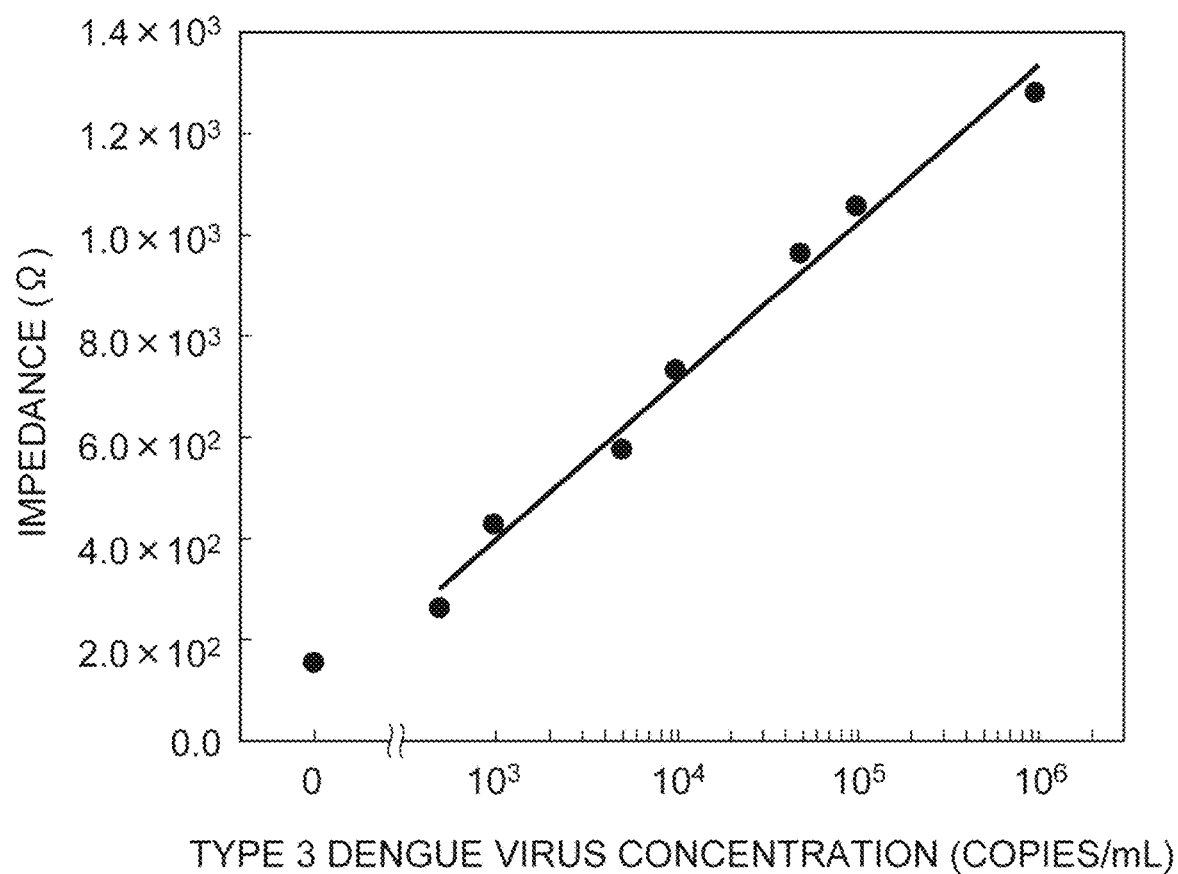
FIG. 11 is a calibration curve created from impedance change rates of Example 9.

DNA-bounded quantum dots in which single-stranded DNA (TCCCTCTCGACATGGAGGAACGTTTTC: SEQ ID No: 1) with 25-base length which is characteristic of type 3 dengue virus was used instead of rabbit anti-G3 hepatitis E virus-like particle IgG antibodies in <Production of Electrode> of the above-described examples were prepared to prepare an electrode for detecting a virus. Single-stranded DNA complementary to SEQ ID No: 1 was used as a specimen. After bonding with DNA in a concentration range of 500 to $10^6$ copies/mL, 20 µM methylene blue was added thereto as a redox indicator, and the impedance was measured through electrochemical impedance spectroscopy (EIS). FIG. 10 shows Nyquist plots showing results obtained from an electrode immersed in a DNA solution at each concentration, and FIG. 11 shows a calibration curve created from the change in impedance obtained from an electrode immersed in a DNA solution at each concentration. The impedance increased as the number of DNA copies increased. The calibration curve showed linearity in the range of the measured concentrations ($R^2=0.985$), and the detection limit was 438 copies/mL.

Example 10

Detection of White Spot Syndrome Virus (WSSV)

Figure 12:
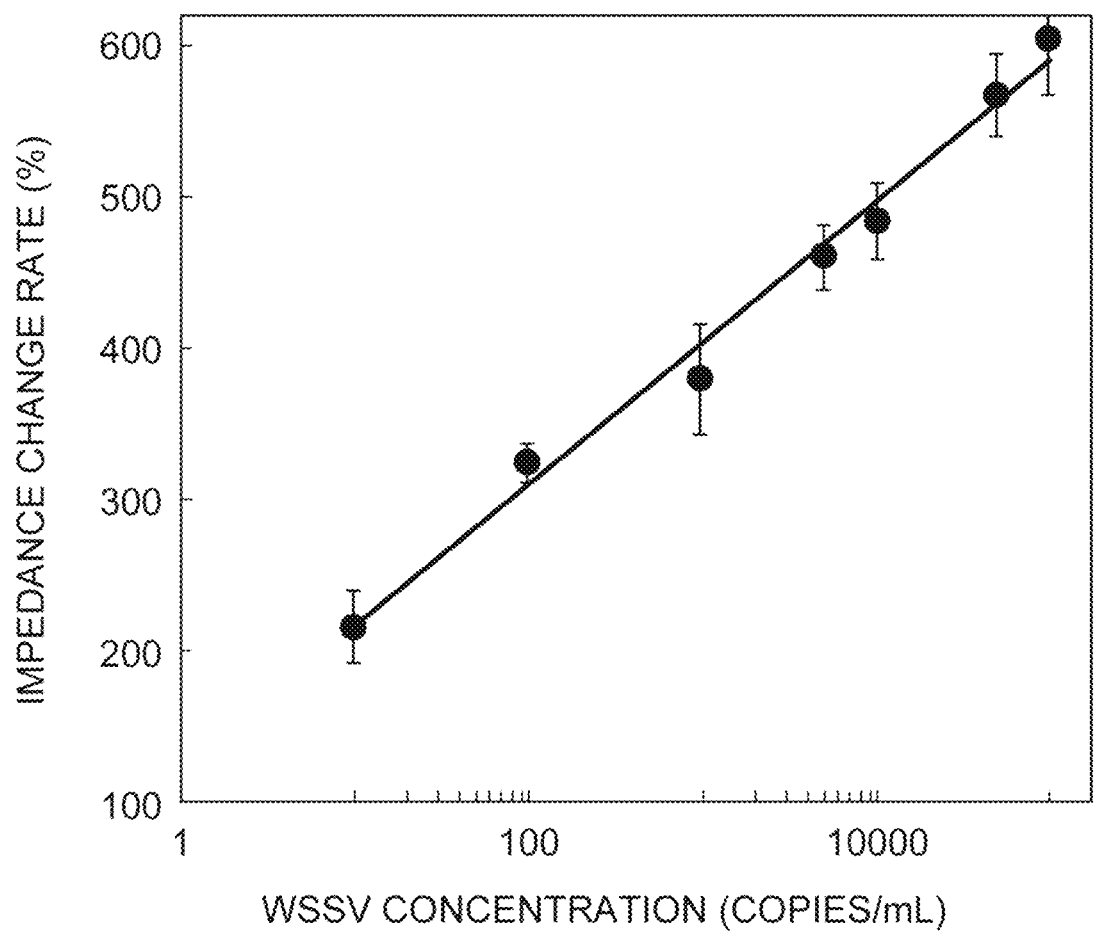
FIG. 12 is a calibration curve created from impedance change rates of Example 10.

A disposable electrode made of silicone rubber was prepared using Anti-WSSV VP28 Antibody (ab26935, Abcam Inc., Cambridge, UK) instead of rabbit anti-G3 hepatitis E virus-like particle IgG antibodies in <Production of Electrode> of the above-described examples to prepare an electrode for detecting a virus. Results obtained by detecting WSSV in a concentration range of 10 to $1.0 \times 10^5$ DNA copies/mL are shown in FIG. 12. The calibration curve showed linearity in the range of the measured concentrations ($R^2=0.9895$), and the detection limit was 78.6 DNA copies/mL

[Sequence List]

What is claimed is:

1. A method for detecting or quantitatively determining a target substance in a sample, the method comprising:
- bringing the sample into contact with an electrode system comprising a working electrode and a counter electrode;
- applying a pulse voltage in the range 0.2-1.2 Volts to the working electrode for a period of time while the working electrode is in contact with the sample;
- moving the working electrode away from the sample after the period of time;
- measuring an impedance of the working electrode,
- wherein the working electrode comprises a complex supported on a surface of an electrode support, and
- wherein the complex comprises a probe for the target substance, a quantum dot which binds to the probe and is doped with nitrogen and sulfur, and a conductive polymer nanowire in which a metal nanoparticle is embedded.

* * * * *

```
SEQUENCE LISTING

<160> NUMBER OF SEQ ID NOS: 1

<210> SEQ ID NO 1
<211> LENGTH: 25
<212> TYPE: DNA
<213> ORGANISM: Dengue virus type 3

<400> SEQUENCE: 1
tcccttcgac atggaggaac gtttc                                          25
```